United States Patent
Novack et al.

(10) Patent No.: US 8,580,238 B2
(45) Date of Patent: Nov. 12, 2013

(54) COSMETIC COMPOSITIONS OF REACTIVELY BLENDED COPOLYMERS

(75) Inventors: Candice DeLeo Novack, Suffern, NY (US); Amitabh Bansal, Hoboken, NJ (US)

(73) Assignee: Avon Products, Inc., New York, NY (US)

( * ) Notice: Subject to any disclaimer, the term of this patent is extended or adjusted under 35 U.S.C. 154(b) by 0 days.

(21) Appl. No.: 13/294,562

(22) Filed: Nov. 11, 2011

(65) Prior Publication Data

US 2013/0121933 A1    May 16, 2013

(51) Int. Cl.
*A61K 8/92*    (2006.01)

(52) U.S. Cl.
USPC ........................................ 424/78.03

(58) Field of Classification Search
None
See application file for complete search history.

(56) References Cited

U.S. PATENT DOCUMENTS

| | | |
|---|---|---|
| 6,025,501 A | 2/2000 | Ulmer et al. |
| 6,492,455 B1 | 12/2002 | Nadolsky |
| 6,706,817 B2 | 3/2004 | Plochocka et al. |
| 2011/0223122 A1 | 9/2011 | Bui et al. |
| 2012/0264852 A1 * | 10/2012 | James et al. ............ 524/10 |

FOREIGN PATENT DOCUMENTS

| | | | |
|---|---|---|---|
| WO | 2008/032342 A1 | 3/2008 | |
| WO | 2008/046763 A1 | 4/2008 | |
| WO | WO 2008/130647 | * 10/2008 | ............ A61K 38/38 |
| WO | 2011/064555 A2 | 6/2011 | |

* cited by examiner

*Primary Examiner* — Brian Gulledge
(74) *Attorney, Agent, or Firm* — David M. Joyal; Joan M. McGillycuddy

(57) ABSTRACT

Provided are cosmetic and personal care compositions having film-formers that are two-phase polymers with a first phase polymer that is a maleated polymer where the maleic anhydride is pendant to the polymer and the second phase polymer is a polymer with complementary reactive groups. The two-phase polymer film former provides enhanced durability benefits for cosmetics, hair care, and skin care products.

23 Claims, 2 Drawing Sheets

COSMETIC COMPOSITIONS OF REACTIVELY BLENDED COPOLYMERS

FIELD OF INVENTION

The present invention relates generally to cosmetic compositions incorporating reactively blended co-polymers as film forming agents to provide long wear benefits to cosmetic, hair care, or skin care products. More specifically, the invention relates to cosmetic compositions that have co-polymers with pendant maleic anhydride functional groups reacted with polymers having complementary functional groups to achieve a compatibilized two-phase film forming system.

BACKGROUND OF THE INVENTION

Lip products, such as lipsticks and lip glosses, are used to impart color and shine to the lips. Most of these conventional lip products are mixtures of waxes, oils, and colorants. A notable drawback to these products is the tendency of the color to transfer from the lips onto a substrate that comes into contact with the lips, including napkins, fingers, clothes, drinking glasses, and the like. Not only does this transfer soil the substrate, but also reduces the vibrancy and durability of the lip products. The user is therefore forced to reapply the product to maintain the desired color and shine. Numerous other cosmetics such as mascaras and foundations, hair products such as temporary colorants, and personal care products such as sunscreens suffer from similar issues with transferability of their colorants or actives.

Efforts to resolve this issue within the field of lip products have been frustrated by trade-offs in increased wear at the expense of comfort and shine. However, some success in imparting longer-wear and transfer resistance to lip products has been achieved through the use of film forming polymers which act to fix the colorants at the site of application and reduce transfer of the product from the lips.

The use of maleic anhydride co-polymers as film formers is known in the art. U.S. Pat. No. 6,492,455 to Nadolsky discloses the use of co-polymers with maleic anhydride functional groups and amine functional polymers as a heat cured coating within cosmetics. The use of maleated olefin copolymers as fixatives for personal care products such as hair sprays is disclosed in U.S. Pat. No. 6,025,501 to Ulmer et al. U.S. Pat. No. 6,706,817 discloses a bioadhesive resulting from a cross-linked maleic anhydride polymer gel. Multiple functionalized maleic anhydride/olefin co-polymers as enhanced film-forming agents are disclosed in PCT Application No. PCT/IT06/00661 to Rando et al. In each of the above-mentioned patents and patent applications, the maleic anhydride group is incorporated into the backbone of the polymer.

However, there is a continuing need in the art for cosmetic film formers that impart desired attributes such as long-wear, transfer resistance, shine, and comfort to the integuments to which the cosmetic is applied.

It is therefore an object of the invention to provide improved cosmetic and personal care products having film formers which, when applied to the surface of an integument, produce films that are long-wearing yet comfortable and which, when used in a pigmented or colored composition, reduce the tendency of the color to transfer from the surface and maintain the desired gloss of the product.

SUMMARY OF THE INVENTION

In accordance with the foregoing objectives and others, it has surprisingly been found that maleic functional polymers having the maleic anhydride within their backbone are not able to form a two-phase co-polymer film upon blending, whereas maleic functional polymers with pendant maleic anhydride functional groups exhibit an enhanced transfer resistance in comparison due to the ability to form two-phase co-polymer films.

In one aspect of the invention, cosmetic compositions are provided for improving the durability of a cosmetic comprising, a suitable cosmetic vehicle, a first phase polymer having pendant maleic anhydride functional groups and a second phase polymer having complementary reactive functional groups, wherein the first phase polymer and second phase polymer are reactively blended to form a two phase co-polymer blend film through an interfacial chemical reaction. In a further embodiment, the first phase polymer and second phase polymer are reactively blended prior to formulation, and in yet another embodiment the first phase polymer and second phase polymer react at the interface during their application to an integument. The durability benefit may be selected from long wear, enhanced transfer resistance, enhanced shine, and/or prolonged exposure to actives.

In another aspect of the invention, the first phase polymer may be comprised of a structure of Formula I:

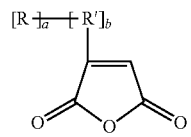

I wherein R and R' are monomer units independently selected from the group consisting of propylene, ethylene, styrene, methacrylate, ester, fluoropolymer, urethane, or any carbon monomer; b is at least 2; and a+b are such that the $M_w$ of the compound is between about 500 and 1,000,000 Daltons. In another embodiment, R and R' are different and may be ethylene and propylene, respectively. The weight ratio of R to R' may be about 40:60 to about 90:10, and more preferably, may be about 45:55 to about 75:25. Further, the maleic anhydride content of the first polymer may be about 0.1-20% by weight, preferably about 1-10% by weight, and most preferably about 2-5% by weight.

In a further embodiment, a+b of the first phase polymer may be such that the $M_w$ of the first phase polymer is between about 10,000 to about 100,000 Daltons, and still further, a+b may be such that the $M_w$ of the first phase polymer is between about 10,000 to about 50,000 Daltons. The first phase polymer has less than about 10% crystallinity.

In yet another aspect of the invention, the second phase polymer is a natural polymer, such as a polysaccharide, or synthetic polymer, such as a siloxane. In a further embodiment of the current invention, the complementary functional groups on the second phase polymer are hydroxyl or amine groups. A representative structure of the second phase polymer is shown as Formula II,

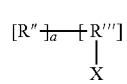

II where R" and R'" are monomer units independently selected from any naturally occurring or synthetic monomer; b is at least 2; and a+b are such that the $M_w$ of the compound is between 500 and 1,000,000 Daltons. R" and R'" may be the same or different, and X is a functional group chosen from either hydroxyl or amine. The complementary reactive functional group content of the second phase polymer may be about 0.1-50% by weight of the second phase polymer, more preferably about 1-20% by weight, and most preferably about 2-10% by weight.

The cosmetic composition may be further comprised of additional ingredients selected from the group consisting of sunscreens, pigments, other film formers, thickeners, retinoids, waxes, emollients, long wearing particles/pigments, and compatible combinations thereof.

A further aspect of the invention relates to a method for imparting a transfer-resistant film on a human integument comprising applying to the human integument an effective amount of the inventive cosmetic composition. In a further embodiment of this method, the first phase polymer and second phase polymer are applied sequentially to the integument and the interfacial reaction occurs during application.

In a further embodiment, the invention relates to a kit comprised of a lip product and a cosmetic composition of the current invention. In a further embodiment of this kit, the first phase polymer and second phase polymer are separate components in the kit.

These and other aspects of the present invention will become apparent to those skilled in the art according to the present description, including the claims.

DETAILED DESCRIPTION

Figure 1:
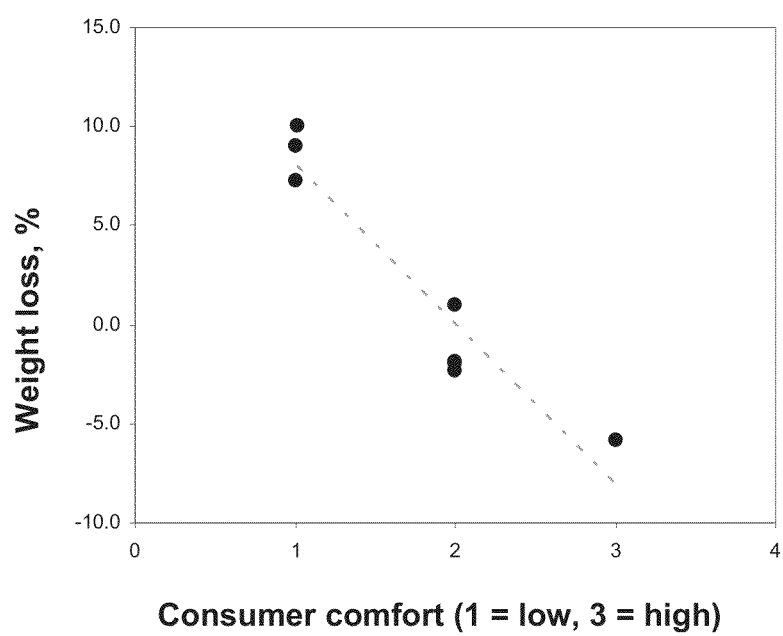
FIG. 1 is a chart illustrating the comfort of commercial lip wear products in comparison to their flexibility validating the assumption that the most flexible products exhibit the greatest comfort.
Figure 2:
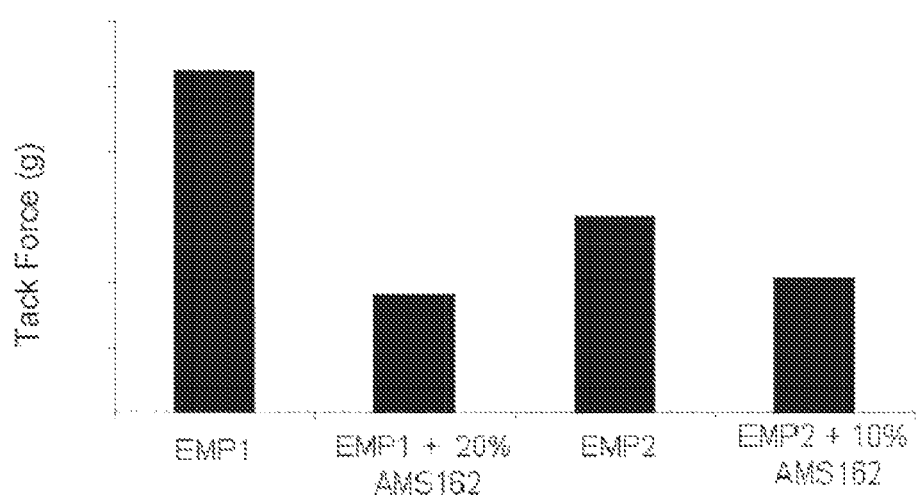
FIG. 2 is a graph illustrating the tack associated with the novel reactively blended co-polymers of the current invention.

U.S. patent application Ser. No. 13/294/,665, titled "Self Emulsified Compositions," filed contemporaneously herewith on Nov. 11, 2011, is incorporated herein by reference in its entirety.

All terms used herein are intended to have their ordinary meaning unless otherwise provided.

As used herein, the term "consisting essentially of" is intended to limit the invention to the specified materials or steps and those that do not materially affect the basic and novel characteristics of the claimed invention, as understood from a reading of this specification. All percentages are by weight based on the total weight of the composition, unless otherwise indicated.

The present invention provides compositions and methods for forming films on human integuments, including, but not limited to, hair of the scalp, eyelashes, skin, and nails.

Generally, the compositions comprise an effective amount of a film forming two-phase co-polymer, i.e., a co-polymer in which the first polymer moiety is not miscible within the second polymer moiety. The film forming two-phase co-polymer has a first phase that is a maleated polymer and a second phase that is a polymer with complementary reactive functional groups, i.e., functional groups capable of reacting with maleic anhydride. An "effective amount" of the two-phase co-polymer is an amount sufficient to measurably increase the durability benefits of the cosmetic on the surface of the integument to which the cosmetic is applied. Typically, an effective amount of a two-phase co-polymer of the current invention will be from about 0.01% to about 70% by weight of the cosmetic composition, more typically from about 5% to about 65% by weight, preferably from about 15% to about 60% by weight, and more preferred still, from about 25% to about 58% by weight. Alternatively, the two-phase polymer may comprise up to about 70% by weight of the cosmetic composition, more preferably up to about 65% by weight of the cosmetic composition, and most preferably up to about 60% by weight of the cosmetic composition.

In particular, the compositions relate to the use of a reactively blended two-phase co-polymer as a film-former within cosmetic compositions. The first phase polymer of the blend is a class of maleated polymers comprising maleic anhydride groups largely pendant to or end capped on the polymer chain rather than polymerized within the backbone of the polymer. The second phase polymer contains complementary functional groups, such as hydroxyl (—OH) or amine (—NH$_2$) groups. The two polymer phases, when blended react at an interface to form and compatibilize the two-phase co-polymer blend of the current invention, or alternatively when applied over one another to form an in-situ bilayer.

The prior art discloses polymeric film forming systems in which the maleic anhydride functionality is within the main chain of the polymer. However, surprisingly, as noted in Example 1 below, maleic functional polymers having the maleic anhydride solely within their backbone are not able to form a two-phase co-polymer film upon blending. Specifically, the inventors note that the maleic anhydride functional groups within the backbone crosslinks the whole bulk resulting in a solid mass rather than a film. Because of this, the liquid and/or flowable film-forming two-phase co-polymer blends of the current invention can exhibit an enhanced transfer resistance in comparison to the known maleic anhydride polymers in which this functionality is within the backbone of the polymer.

Maleated and amine functional polymers adhere to skin well and provide long wear properties. Without wishing to be bound to a particular theory, the inventors of the current invention believe that the film forming co-polymers of the current invention provide long term wear because (1) the maleic anhydride of the first phase polymer reacts with the complementary functional group of the second phase polymer to compatibilize the two-phase co-polymer blend; (2) any excess maleic anhydride groups increase adhesion with the skin anchoring the resulting film to the integument; and (3) the flexible polymer chains of the first phase polymer provide smooth and flexible texture to the film. These benefits are achieved in the presence of a small amount of maleic anhydride, and may be used to compatibilize polyolefins with silicones.

The maleated polymers of the current invention generally include alkane homopolymers, such as polyisoprene, polybutadiene, polypropylene, or polyethylene, or co-polymers of varying alkane monomer units. In an illustrative embodiment of the invention, the first phase polymer is a maleated polymer generally of Formula I:

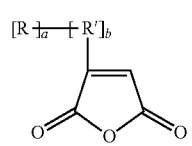

I wherein R and R' are monomer units independently selected from propylene, ethylene, styrene, methacrylate, ester, fluoropolymer, urethane, or any carbon monomer; and b is at least 2.

In an embodiment, R may be the same monomer unit as R' to generate a maleated homopolymer. In a preferred embodiment, R and R' are different monomers to form a maleated co-polymer. Preferably, R and R' are different, and more preferably they are selected from either propylene or ethylene to form a maleated co-polymer of the current invention.

In a further embodiment, the weight ratio of R:R' may be from about 1:100 to 100:1, preferably about 40:60 to 90:10, and most preferably in the range of about 75:25. Thus, in the preferred maleated ethylene propylene co-polymer of the current invention the weight ratio of ethylene:propylene varies from 1:100 to 100:1, but is more preferably in the range of about 40:60 to 90:10, and most preferably in the range of 45:55 to 75:25.

As noted above, b is at least 2 and thus the maleated polymers of the current invention are multifunctional, i.e., having more than one maleic anhydride functional group attached to the polymer, and may be bifunctional, bifunctional, etc. In a further embodiment of the current invention, the maleic anhydride content is about 0.1-20% by weight, more preferably about 1-10% by weight, and most preferably about 2-5% by weight of the first phase polymer.

The molecular weight (weighted molecular weight ($M_w$)) of the copolymer will typically be in the range of about 500 to 1,000,000 Daltons, but should ideally be such that the polymer is liquid or semi-solid at room temperature, rather than solid. In one embodiment, the molecular weight of the copolymer will be between about 1,000 and 500,000, or between about 5,000 and 100,000 Daltons, or between about 10,000 and about 50,000 Daltons. Additionally, a+b of the maleated polymer are selected such that the $M_w$ of the polymer is between about 5,000 and 100,000 Daltons, and most preferably between about 10,000 and 50,000 Daltons.

In one embodiment, the first phase maleated polymer is substantially non-crystalline with less than about 10% crystallinity, in a preferred embodiment the maleated polymer may have less than about 2% crystallinity to no crystallinity at all.

Commercially available polymers that may act as a first phase polymer may include, but are not limited to, Marlene CP-80 (Lion Copolymer), an Ethylene/Maleic anhydride/Propylene Copolymer, Exxelor (ExxonMobil), a maleic anhydride functionalized polypropylene, and/or Amplify (The Dow Chemical Company), a maleic anhydride grafted polyethylene.

The first phase polymer may comprise about 0.1% to 50% by weight of the cosmetic composition, preferably about 5% to 48% by weight, most preferably about 10% to about 45% by weight.

A representative structure of the second phase polymer is shown as Formula II,

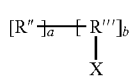

II where R" and R'" are monomer units independently selected from any naturally occurring or synthetic monomer; b is at least 2; and a+b are such that the $M_w$ of the compound is between about 500 and 1,000,000 Daltons. R" and R'" may be the same or different and X is a functional group chosen from either hydroxyl or amine. The complementary reactive functional group content of the second phase polymer may be about 0.1-50% by weight of the second phase polymer, more preferably about 1-20% by weight, and most preferably about 2-10% by weight.

Suitable naturally occurring polymers may include, but are not limited to, polysaccharides such as pullan, carrageen, glycon, hydroxycellulose, amylose, chitosan, N,O-carboxymethylchitosan, algin and alginic acid, starch, dextran, cyclodextrin, konjac glucomannan, chitin, pustulan, heparin, cardlan, hyaluronic acid, xantham, and combinations and derivatives thereof. R" and R'" may include, but are not limited to, natural monomers comprising the above-noted naturally occurring polymers as well as monosaccharaides or sugars such as aldose, glucose, galactose, xylose, ribose, tetroses, pentoses, hexoses, and combinations and derivatives thereof. Suitable synthetic polymers for the second phase polymer may include, but are not limited to, polyolefins; polyether such as polyethylene glycol, polypropylene glycol, polytetramethylene glycol, polytetramethylene ether glycols, polyethylene oxide, or polypropylene oxide; polyester; polysiloxane such as polydimethylsiloxane, amidomethicones, or phenyltrimethicones; polyamide; polyacrylate such as sodium polyacrylate, carbomers, or carbapols; polyurethane; polyphosphazene; polyvinylpyrolidone; mixtures or combinations thereof.

R" and R'" may include, but are not limited to, synthetic monomers including, but not limited to those that comprise the above-noted synthetic polymers as well as olefins such as ethylene, propylene, butane, or methylpentane; amides, or acrylic monomers such as methyl acrylate, ethyl acrylate, 2-chloroethyl vinyl ether, 2-ethylhexyl acrylate, hydroxyethyl methacrylate, butyl acrylate, or butyl methacrylate; styrene, ester, fluoropolymer, urethane, siloxane, or any carbon monomer. Preferably, the second phase polymer is a polysiloxane. The polymers for the second phase polymer may include linear or branched versions of the above noted polymers. In one embodiment, R" may be the same monomer unit as R'" to generate a homopolymer. In a preferred embodiment, R" and R'" are different monomers to form a co-polymer.

The complementary functional groups of the second phase polymer may be pendant to, end capped on, and/or within the backbone of the second phase polymer chain. The functional content in the second phase polymer may vary from about 0.1-50% by weight of the second phase polymer, but is more preferably in the 1-20% range and most preferably in the 2-10% range, such that the number of functional groups per polymer chain is at least 2. In further embodiments, the multiple functional groups may be the same or different, i.e., amine and amine, hydroxyl and hydroxyl, amine and hydroxyl, etc.

In a further embodiment of the second phase polymer, the polymer may be further substituted with simple sugars to enhance the moisturizing effect of the cosmetic composition. Suitable simple sugars may include, but not limited to, D-glucose, D-mannose, D- and L-galactose, D-xylose, L-arabinose, D-glucoronic acid, D-galactoronic acid, D-mannuronic acid, D-glucosamine, D-galactosamine, neuraminic acid, and combinations and derivatives thereof.

As with the first phase polymer, the molecular weight of the second phase polymer will typically be such that the polymer is liquid or semi-solid at room temperature, rather than solid. The molecular weight (weighted molecular weight Mw) of the second phase polymer will typically be in the range of about 500 to 1,000,000 Daltons, but should ideally be such that the polymer is liquid or semi-solid at room temperature, rather than solid. In one embodiment, the molecular weight of the copolymer will be between about 1,000 and 500,000 Daltons, between about 5,000 and 100,000 Daltons, between about 10,000 and 50,000 Daltons, or between about 10,000 and 25,000 Daltons.

Commercially available polymers suitable for use as second phase polymers may include, but are not limited to, AMS-162 and AMS-132 (Gelest, Inc.), amino propyl polydimethylsiloxanes, and KF8004 (Shin Etsu Inc.), amodimethicones, and/or PEG 8 (The Dow Chemical Company), a Carbowax PEG 400.

The second polymer may comprise about 0.1% to 35% by weight of the cosmetic composition, preferably about 2% to 25%, and most preferably about 5% to 20%.

The first phase polymer and second phase polymer may then be admixed to form the two-phase reactive co-polymer blend. The first phase polymer and second phase polymers react at the interface of the two polymers to crosslink and thereby compatibilize the two-phase co-polymer blend. This reaction may occur prior to the addition of the polymers to a cosmetic formulation, coextensively with the development of the formulation, or sequentially during application to the integument—i.e., one phase is laid down on the integument followed by the second phase in order to form a cross-linked bilayer in situ.

These reactions may be formed at temperatures ranging from 20° C. to 100° C., preferably about 20° C. to about 75° C., and most preferably about 20° C. to about 50° C. Similarly, the reaction will proceed at pHs of about 1 to 14, more preferably about 4 to 9.5 and most preferably about 5 to 8. Ideally, the reaction will proceed under ambient conditions without the need for catalysts or activators.

In some, but not all, embodiments, the compositions may include additional film-forming polymers. Particular mention may be made of polymers that provide good transfer-resistance, including silicone acrylate copolymers, such as those having the INCL names Butyl Acrylate/Hydroxypropyl Dimethicone Acrylate Copolymer (CTFA Monograph ID 12998), Acrylates/Dimethicone Copolymer (CTFA Monograph ID 10082), and Acrylates/Ethylhexyl Acrylate/Dimethicone Methacrylate Copolymer (CTFA Monograph ID 16592). Other suitable film formers include, without limitation, polyolefins, polyamides, polyesters, polyimides, polyurethanes, acrylates, and the like.

In some embodiments, the compositions may include from about 0.1% to about 50%, typically from about 1% to about 20%, by weight of a wax component. The waxes may be low melt waxes such as higher chain alkanes, including for example, n-octadecane (MP~28-30° C.), n-nonadecane (MP~32° C.), and n-eicosane (MP~37° C.), or high melt waxes including, without limitation, many traditional waxes that are derived, for example, from animals, insects, vegetables, minerals, or petroleum, as well as synthetic waxes, Fisher Tropsch waxes, and mixtures of any of the foregoing waxes. Specific mention is made of carnauba, paraffin wax, candelilla, castor, beeswax, microcrystalline wax, ceresin, ozokerite, polyethylene wax, low MW polyalkyacrylate, and silicone waxes, such as alkyl silicones, or any combinations thereof.

The two-phase co-polymer reactive blends of the current invention form films that provide durability benefits to cosmetic, hair care, and skin care products. The durability benefits may include, but are not limited to, long wear, enhanced transfer resistance, reduced tack, and/or prolonged exposure to actives. As used herein, the term "long-wear" means that the composition retains a freshly applied appearance for an extended period of time, for example, at least six hours, at least eight hours, at least twelve hours, even fourteen hours or more, under conditions of normal use. A film is transfer-resistant if it displays a decreased propensity to transfer colorant to a substrate on contact therewith as compared to an otherwise identical composition in the absence of the film-former. Preferably, the films of the invention are also comfortable, which means that they are elastic and do not pull tightly on the hair, skin or lips. The comfort may be measured on the basis of consumer or expert panel testing as is well known in the cosmetics field.

The inventive compositions will comprise a cosmetically acceptable vehicle. By "cosmetically acceptable" is meant that the vehicle is safe for contact with a human integument.

The inventive compositions may be useful in a variety of applications including cosmetics such as lipstick, lip glosses, lip colors, waterproof mascaras, transfer-resistant foundations, nail enamels and nail care products; hair care products such as shampoos, conditioners, styling gels, creams, mousses, and/or sprays; and skin care products such as waterproof sunscreen, sunblock, insect repellants, anti-aging creams, ointments, anti-acne creams, and moisturizers. It is contemplated that any cosmetically acceptable vehicle known in the art will be useful for these formulations and one of ordinary skill in the art is capable of selecting the appropriate vehicle for the intended use.

The vehicle may comprise water or hydrophobic or hydrophilic organic solvents. Suitable hydrophilic solvents include but are not limited to, alcohols (e.g., ethanol, isopropanol, benzyl alcohol, phenylethyl alcohol, etc.), propylene glycol, butylene glycol, pentylene glycol, hexylene glycol, caprylyl glycol, glycerin, carbitol, glycol ethers such as, for example, ethylene glycol monomethyl, monoethyl and monobutyl ethers, ethers of propylene glycol such as, for example, propylene glycol monomethyl ether, dipropylene glycol and diethylene glycol alkyl ethers such as, for example, diethylene glycol monoethyl ether or monobutyl ether, and or any combinations thereof.

Suitable hydrophobic vehicles include hydrocarbon oils, which may be saturated or unsaturated, have an aliphatic character and be straight or branched chained or contain alicyclic or aromatic rings. Essentially any oil is contemplated to be useful, although highly hydrophobic oils are preferred. Suitable non-limiting examples include vegetable oils; esters such as octyl palmitate, isopropyl myristate and isopropyl palmitate; ethers such as dicapryl ether; fatty alcohols such as cetyl alcohol, stearyl alcohol and behenyl alcohol, isoparaffins such as isooctane, isododecane and isohexadecane; silicone oils such as dimethicones, cyclic silicones, and polysiloxanes; hydrocarbon oils such as mineral oil, petrolatum, isoeicosane and polyisobutene; natural or synthetic waxes; and the like.

Suitable hydrophobic hydrocarbon oils may be saturated or unsaturated, have an aliphatic character and be straight or branched chained or contain alicyclic or aromatic rings. Hydrocarbon oils include those having 6-20 carbon atoms, more preferably 10-16 carbon atoms. Representative hydrocarbons include decane, dodecane, tetradecane, tridecane, and $C_{8-20}$ isoparaffins. Paraffinic hydrocarbons are available from Exxon under the ISOPARS trademark, and from the Permethyl Corporation. In addition, $C_{8-20}$ paraffinic hydrocarbons such as C isoparaffin (isododecane) manufactured by the Permethyl Corporation having the tradename Permethyl 99™ are also contemplated to be suitable. Various commercially available $C_{16}$ isoparaffins, such as isohexadecane (having the tradename Permethyl R™) are also suitable. Examples of preferred volatile hydrocarbons include polydecanes such as isododecane and isodecane, including for example, Permethyl-99A (Presperse Inc.) and the $C_7$-$C_8$ through $C_{12}$-$C_{15}$ isoparaffins such as the Isopar Series available from Exxon Chemicals. A representative hydrocarbon solvent is isododecane.

The vehicle may comprise a silicone oil phase which may include volatile silicone oils, non-volatile silicone oils, and combinations thereof. By volatile silicone oil is meant that the oil readily evaporates at ambient temperatures. Typically, volatile silicone oils will exhibit a vapor pressure ranging from about 1 Pa to about 2 kPa at 25° C.; will preferably have a viscosity of from about 0.1 to about 10 centistokes, preferably about 5 centistokes or less, more preferably about 2 centistokes or less, at 25° C.; and will boil at atmospheric pressure at from about 35° C. to about 250° C.

Volatile silicones include cyclic and linear volatile dimethylsiloxane silicones. In one embodiment, the volatile silicones may include cyclodimethicones, including tetramer (D4), pentamer (D5), and hexamer (D6) cyclomethicones, or mixtures thereof. Particular mention may be made of the volatile cyclomethicone-hexamethyl cyclotrisiloxane, octamethyl-cyclotetrasiloxane, and decamethyl-cyclopentasiloxane. Suitable dimethicones polymers are available from Dow Corning under the name Dow Corning 200® Fluid and have viscosities ranging from 0.65 to 600,000 centistokes or higher. Suitable non-polar, volatile liquid silicone oils are disclosed in U.S. Pat. No. 4,781,917, herein incorporated by reference in its entirety. Additional volatile silicones materials are described in Todd et al., "Volatile Silicone Fluids for Cosmetics", Cosmetics and Toiletries, 91:27-32 (1976), herein incorporated by reference in its entirety. Linear volatile silicones generally have a viscosity of less than about 5 centistokes at 25° C., whereas the cyclic silicones have viscosities of less than about 10 centistokes at 25° C. Examples of volatile silicones of varying viscosities include Dow Corning 200, Dow Corning 244, Dow Corning 245, Dow Corning 344, and Dow Corning 345, (Dow Corning Corp.); SF-1204 and SF-1202 Silicone Fluids (G.E. Silicones), GE 7207 and 7158 (General Electric Co.); and SWS-03314 (SWS Silicones Corp.). Linear, volatile silicones include low molecular weight polydimethylsiloxane compounds such as hexamethyldisiloxane, octamethyltrisiloxane, decamethyltetrasiloxane, and dodecamethylpentasiloxane to name a few.

Non-volatile silicone oils will typically comprise polyalkylsiloxanes, polyarylsiloxanes, polyalkylarylsiloxanes, or mixtures thereof. Polydimethylsiloxanes are preferred non-volatile silicone oils. The non-volatile silicone oils will typically have a viscosity from about 10 to about 60,000 centistokes at 25° C., preferably between about 10 and about 10,000 centistokes, and more preferred still between about 10 and about 500 centistokes; and a boiling point greater than 250° C. at atmospheric pressure. Non limiting examples include dimethyl polysiloxane (dimethicone), phenyl trimethicone, and diphenyldimethicone.

The vehicle may comprise a single phase, a dual-phase system, or an emulsion. The emulsion may be oil-in-water, water-in-oil, water-in-silicone, silicone-in-water, or hydrocarbon oil-silicone oil. Where the product is intended as a spray, it may be desirable to employ a single phase vehicle, or a dual phase vehicle comprising an aqueous phase and an oil phase, the oil phase comprising a hydrocarbon oil or a silicone oil. Alternatively, it is contemplated that the vehicle may be anhydrous. The anhydrous vehicle preferably comprises a silicone oil. It is to be understood that the term "anhydrous" as used herein typically refers to a composition comprising at most 5% water, more typically to a composition comprising at most 1% water, and usually a composition comprising an amount of water absorbed from ambient conditions.

Non-limiting examples of suitable emulsions include water-in-oil emulsions, oil-in-water emulsions, silicone-in-water emulsions, water-in-silicone emulsions, wax-in-water emulsions, water-oil-water double emulsions or the like having the appearance of a cream, gel or microemulsions. The oil and silicone phases of the emulsions may be derived from the oils and silicones disclosed above. When formulated as an emulsion, an emulsifier such as a nonionic, anionic or amphoteric surfactant, is typically included.

The water phase of the emulsion preferably has one or more organic compounds, including humectants (such as propylene glycol and glycerin); other water-dispersible or water-soluble components including thickeners such as veegum or hydroxyalkyl cellulose; gelling agents, such as high $M_w$ polyacrylic acid, i.e. CARBOPOL 934; and mixtures thereof. The emulsion may have one or more emulsifiers capable of emulsifying the various components present in the composition.

The oil phase may comprise one or more waxes, including for example, rice bran wax, carnauba wax, ouricurry wax, candelilla wax, montan waxes, sugar cane waxes, ozokerite, polyethylene waxes, Fischer-Tropsch waxes, beeswax, microcrystalline wax, silicone waxes, fluorinated waxes, and any combination thereof. The oil phase may comprise one or more volatile and/or non-volatile silicone oils disclosed above as well.

Non-limiting emulsifiers included emulsifying waxes, emulsifying polyhydric alcohols, polyether polyols, polyethers, mono- or di-ester of polyols, ethylene glycol mono-stearates, glycerin mono-stearates, glycerin di-stearates, silicone-containing emulsifiers, soya sterols, fatty alcohols such as cetyl alcohol, fatty acids such as stearic acid, fatty acid salts, and mixtures thereof. The preferred emulsifiers include soya sterol, cetyl alcohol, stearic acid, emulsifying wax, and mixtures thereof. Other specific emulsifiers that can be used in the composition of the present invention include, but are not limited to, one or more of the following: sorbitan esters; polyglyceryl-3-diisostearate; sorbitan monostearate, sorbitan tristearate, sorbitan sesquioleate, sorbitan monooleate; glycerol esters such as glycerol monostearate and glycerol monooleate; polyoxyethylene phenols such as polyoxyethylene octyl phenol and polyoxyethylene nonyl phenol; polyoxyethylene ethers such as polyoxyethylene cetyl ether and polyoxyethylene stearyl ether; polyoxyethylene glycol esters; polyoxyethylene sorbitan esters; dimethicone copolyols; polyglyceryl esters such as polyglyceryl-3-diisostearate; glyceryl laurate; Steareth-2, Steareth-10, and Steareth-20, to name a few. Additional emulsifiers are provided in the INCI Ingredient Dictionary and Handbook 11th Edition 2006, the disclosure of which is hereby incorporated by reference.

These emulsifiers typically will be present in the composition in an amount from about 0.001% to about 10% by weight, in particular in an amount from about 0.01% to about 5% by weight, and more preferably, below 1% by weight.

The water-in-silicone emulsion may be emulsified with a nonionic surfactant (emulsifier) such as, for example, polydiorganosiloxane-polyoxyalkylene block copolymers, including those described in U.S. Pat. No. 4,122,029, the disclosure of which is hereby incorporated by reference. These emulsifiers generally comprise a polydiorganosiloxane backbone, typically polydimethylsiloxane, having side chains comprising -(EO)$_m$— and/or —(PO)$_n$— groups, where EO is ethyleneoxy and PO is 1,2-propyleneoxy, the side chains being typically capped or terminated with hydrogen or lower alkyl groups (e.g., $C_{1-6}$, typically $C_{1-3}$). Other suitable water-in-silicone emulsifiers are disclosed in U.S. Pat. No. 6,685,952, the disclosure of which is hereby incorporated by reference herein. Commercially available waterin-silicone emulsifiers include those available from Dow Corning under the trade designations 3225C and 5225C FORMULATION AID; SILICONE SF-1528 available from General Electric; ABIL EM 90 and EM 97, available from Goldschmidt Chemical Corporation (Hopewell, Va.); and the SILWET series of emulsifiers sold by OSI Specialties (Danbury, Conn.).

Examples of water-in-silicone emulsifiers include, but are not limited to, dimethicone PEG 10/15 crosspolymer, dimethicone copolyol, cetyl dimethicone copolyol, PEG-15 lauryl dimethicone crosspolymer, laurylmethicone crosspolymer, cyclomethicone and dimethicone copolyol, dimethicone copolyol (and) caprylic/capric triglycerides, polyglyceryl-4 isostearate (and) cetyl dimethicone copolyol (and) hexyl laurate, and dimethicone copolyol (and) cyclopentasiloxane. Preferred examples of water-in-silicone emulsifiers include, without limitation, PEG/PPG-18/18 dimethicone (trade name 5225C, Dow Corning), PEG/PPG-19/19 dimethicone (trade name BY25-337, Dow Corning), Cetyl PEG/PPG-10/1 dimethicone (trade name Abil EM-90, Goldschmidt Chemical Corporation), PEG-12 dimethicone (trade name SF 1288, General Electric), lauryl PEG/PPG-18/18 methicone (trade name 5200 FORMULATION AID, Dow Corning), PEG-12 dimethicone crosspolymer (trade name 9010 and 9011 silicone elastomer blend, Dow Corning), PEG-10 dimethicone crosspolymer (trade name KSG-20, Shin-Etsu), and dimethicone PEG-10/15 crosspolymer (trade name KSG-210, Shin-Etsu).

The water-in-silicone emulsifiers typically will be present in the composition in an amount from about 0.001% to about 10% by weight, in particular in an amount from about 0.01% to about 5% by weight, and more preferably, below 1% by weight.

The aqueous phase of the emulsion may include one or more additional solvents, including lower alcohols, such as ethanol, isopropanol, and the like. The volatile solvent may also be a cosmetically acceptable ester such as butyl acetate or ethyl acetate; or the like.

The oil-containing phase will typically comprise from about 10% to about 99%, preferably from about 20% to about 85%, and more preferably from about 30% to about 70% by weight, based on the total weight of the emulsion, and the aqueous phase will typically comprise from about 1% to about 90%, preferably from about 5% to about 70%, and more preferably from about 20% to about 60% by weight of the total emulsion. The aqueous phase will typically comprise from about 25% to about 100%, more typically from about 50% to about 95% by weight water.

The cosmetic vehicle may be thickened through the addition of various thickeners. The thickener may be nonionic, cationic, anionic or amphoteric. Preferably, the thickener is a cationic thickener, including without limitation cationic conditioning polymers. Suitable cationic polymers include, but are not limited to, cationized cellulose, cationized guar gum, diallyly quaternary ammonium salt/acrylamide copolymers, polyquaternium-37, and mixtures thereof. Among the various cationic thickeners, special mention may be made of polyquaternium-37 (INCI).

Other suitable thickeners can include, for example, acrylic acid homopolymers (sold under the trade name CARBOPOL® by Lubrizol Corp.), acrylates/$C_{10-30}$ alkyl acrylate crosspolymer (available under the trade names CARBOPOL® 1342 and 1382; and PEMULINS® TR-1 and TR-2 from BF Goodrich), Acrylates/Steareth-20 Itaconate copolymer (available under the trade name STRUCTURE® 2001 from National Starch), Acrylates/Ceteth-20 Itaconate copolymer (available under the trade name STRUCTURE® 3001 from National Starch), bentonite, PVM/MA Decadiene Crosspolymer, which is a crosspolymer of methylvinylether/maleic anhydride copolymer cross-linked with 1, 9 decadiene (commercially available under the trade name STABILEZE® QM from International Specialties Products), Acrylates/steareth-20 methacrylate copolymer (sold under the trade name ACRYSOL™ ICS-1 by Rohm and Haas Co.), acrylamide/sodium acrylate copolymer (sold under the trade name HOSTACERIN® PN 73 by Hoecsht AG), acrylate copolymer (sold under the trade name ANTIL 208 by Goldschmidt), acrylic acid/acrylonitrogens copolymer (sold under the trade names HYPAN® SA-100H, SR-150H supplied by Lipo), Acrylic/acrylate copolymer (sold under the trade names CARBOSET® 5 514, 515, 525, XL-19, XL-19×2, X1-28, XL-40, 526 by BF Goodrich), Ammonium acrylates/acrylonitrogens copolymer (sold under the trade name HYPAN® SS-201 by Lipo), Quaternium-18 Bentonite, which is a sodium salt of crosslinked poly(acrylic acid) (sold under the tradenames PNC 430, PNC 410, PNC 400 by 3V), Stearalkonium Bentonite (sold under the trade name CLAYTON® by Southern Clay Products), Quaternium-18 Hectorite (Bentone 38), Stearalkonium Hectorite (Bentone 27), Poly(acrylic acid) (sold under the trade names CARBOPOL® 400 by BF and AQUATREAT® by Alco), trihydroxystearin (commercially available under the trade names THIXICIN® by Rheox and FLOWTONE™ by Southern Clay Products), Dimethylaminoethyl methacrylamide and acrylamide copolymer (SALCARE® SC63 from Ciba Specialties), Acrylic polymer anionic or cationic thickening agents (sold under the trade name SYNTHALEN™ by 3V), Polyacrylate-1 crosspolymer (INCI) (sold under the trade name CARBOPOL® Aqua CC by Lubrizol Corp.), Sodium Acrylate copolymer (sold under the trade name TINOVIS® ADM by Ciba), and Polyacrylamidomethylpropane Sulfonic Acid (sold under the trade name Cosmedia HSP-1180 by Cognis Care Chemicals).

The thickener preferably comprises from about 0.001 to about 25%, more preferably at about 0.1% to about 15%, and more preferred still from about 0.5% to about 5% by weight of the vehicle.

The compositions of the invention may optionally comprise other active and inactive ingredients typically associated with cosmetic, hair care, or skin care products. The nature of these other ingredients and their amounts should preferably be suitable for formulating a stable product which incorporates the two-phase co-polymer reactive blends and imparts the durability benefits of the current invention. It is within the skill in the art to choose additional active and/or inactive ingredients for a cosmetic, hair care, and/or skin care product. Suitable other ingredients include, but are not limited to, excipients, fillers, emulsifying agents, antioxidants, surfactants, film formers, chelating agents, gelling agents, waxes, thickeners, emollients, humectants, moisturizers, vitamins; minerals, viscosity and/or rheology modifiers, sunscreens, keratolytics, depigmenting agents, retinoids, alpha-hydroxy acids, antibacterial agents, antifungal agents, antimicrobials, antivirals, anti-acne agents, skin cooling compounds, skin protectants, skin penetration enhancers, exfollients, fragrances, depigmenting agents, self-tanning agents, preservatives, stabilizers, amino acids, antioxidants, chelating agents, colorants, emollients, photostabilizing agents (e.g., UV absorbers), preservatives, stabilizers, staining agents, and mixtures thereof. It is contemplated that the cosmetic compositions, when formulated for use as a hair care product, can also include anti-dandruff, deodorant, and/or antiperspirant ingredients.

The two-phase co-polymer reactive blends of the current invention exhibit shine suitable for various cosmetic applications such as lip sticks and glosses. The cosmetic compositions of the invention may optionally include one or more agents that further provide or enhance shine. Shine enhancing agents will typically have a refractive index greater than about 1.4, preferably greater than about 1.5 when measured as a film at 25° C. Suitable shine enhancing agents include without limitation, polyols (e.g., glycerin), fatty esters, silicone oils, phenylpropyldimethylsiloxysilicate, polybutene, polyisobutene, hydrogenated polyisobutene, hydrogenated polycyclopentadiene, propyl phenyl silsesquioxane resins; lauryl methicone copolyol, perfluorononyl dimethicone, dimethicone/trisiloxane, methyl trimethicone, and combinations thereof. In one embodiment, the composition will comprise a shine-enhancing agent in an amount from about 0.1% to about 10% by weight, more preferably from about 1% to about 5% by weight, based on the total weight of the composition.

In some embodiments, the compositions further comprise a colorant. As used herein, the term "colorant" includes any material added to impart a hue or optical effect to the composition, and includes without limitation pigments, pearls, lakes, and dyes. The composition may comprise colorants in an amount from about 0.1% to about 90% based on the entire weight of the composition, but typically will comprise from about 0.5% to about 20% by weight, and more typically from about 1% to about 10% by weight colorants.

Suitable colorants are well known in the art and are disclosed in the C.T.F.A. Cosmetic Ingredient Handbook, First Edition, 1988, the contents or which are hereby incorporated by reference. Organic dyes include, for example, FD&C dyes and D&C dyes. Lakes include those based on barium, strontium, calcium or aluminum. Exemplary inorganic pigments include, but are not limited to, metal oxides and metal hydroxides such as iron oxides, iron hydroxides, titanium dioxide, zirconium oxides, cerium oxides, chromium oxides, chromium hydroxides, manganese oxides, and zinc oxides. Other suitable colorants include carbon black, ultramarine blue, ferric blue, Prussian blue, manganese violet, talc, mica, sericite, calcium carbonate, fumed silica, and the like. Suitable pearling pigments include, without limitation, bismuth oxychloride, guanine, and titanated mica. The colorants may be surface modified, for example with Triethoxy Caprylylsilane, to adjust one or more characteristics of the colorant, such as dispersibility in the vehicle.

In some embodiments, the colorant will comprise an alkyl silane surface-treated colorant comprising an alumina substrate (e.g., platelet shaped) and a pigment, dye, or lake bonded to the alumina substrate by an alkyl silane surface treatment. Typically, the alkyl silane will be octylsilane and may be formed by treatment with Triethoxy Caprylylsilane. Non-limiting examples of such colorants include, but are not limited to, the COVALUMINE™ line by SENSIENT™ Cosmetic Techologies LCW.

Additionally, sunscreens may also be added to the cosmetic composition of the current invention. The cosmetic composition of the current invention may increase the effectiveness of the sunscreen by fixing it in place over the keratinaceous integument to which it is applied. Alternatively, the sunscreen may be added to the cosmetic composition when it is used to enhance the color retention of artificial hair coloring to additive or synergistic effect as the sunscreen may counteract environmental stresses on the coloring. Non-limiting examples of sunscreens include benzophenones, bornelone, butyl paba, cinnamidopropyl trimethyl ammonium chloride, disodium distryrylbiphenyl disulfonate, paba, potassium methoxycinnamate, butyl methoxydibenzoylmethane, octyl methoxycinnamate, oxybenzone, octocrylene, octyl salicylate, phenylbenzimidazole sulfonic acid, ethyl hydroxypropyl aminobenzoate, menthyl anthranilate, aminobenzoic acid, diethanolamine methoxycinnamate, glyceryl aminobenzoate, octylmethoxycinnamate, titanium dioxide, zinc oxide, cinoxate, oxybenzone, Padimate O, red petrolatum, and mixtures thereof.

Commercial applications for cosmetics may include, but are not limited to, long wear lipsticks, lip glosses, lip colors, smudge-free mascara, or transfer resistant foundations. Commercial applications for the cosmetic composition of the current invention may include hair care products, such as shampoos, conditioners, hair leave in treatments (e.g., color protection), and hair styling products, such as gels, creams, mousses, and sprays. Commercial application within skin care products may include applications such as and long lasting SPF, insect repellant, long lasting moisturizers, anti-aging/wrinkle creams, or anti-acne creams. A further commercial application for the cosmetic compositions of the current invention may be directed to body paints.

The present invention provides a method for improving long wear and transfer resistance in a cosmetic comprising applying to a human integument a cosmetic composition having a two-phase co-polymer reactive blend of the current invention in a suitable vehicle. The methods and composition may be applied to any integument that may benefit from a water/oil resistant film. For example, a cosmetic composition incorporating the two-phase co-polymer reactive blend may be applied over a lipstick to reduce color transference of the lipstick. Further, the cosmetic compositions of the current invention may be incorporated into the hair styling, cosmetic or skin care product so that the film is formed contemporaneously with the application of the product.

The present invention also provides kits or prepackaged materials containing the compositions of the present invention. These kits or prepackaged materials can provide the two-phase co-polymer reactive blends mixed directly into a cosmetic, hair care, and/or skin care product, provided separately, but in the same package as the cosmetic, hair care, or skin care composition, which then can be premixed and applied to the integument; or provided as a separate first phase polymer and a separate second phase polymer to be applied sequentially to the integument to develop a cross-linked bilayer in situ over the integument. Likewise, the two-phase co-polymer reactive blends of the current cosmetic composition may be a prepackaged kit coupled to one or more hair treatment compositions (e.g., shampoos, conditioners, and others as described herein and known in the art), cosmetics (e.g., lip stick, lip gloss, mascara, and others as described herein and known in the art), or skin care products (e.g., sunblocks, anti-aging creams, and others as described herein and known in the art). These kits may further include documentation related to the cosmetic composition of the current invention including, but not limited to, instructions for use, ingredient lists, and or warnings.

The following examples are meant to demonstrate certain aspects of the invention in a non-limiting fashion.

EXAMPLES

Example 1

Transfer Resistance

The following materials were tested for transfer resistance.

TABLE 1

| | Materials used | | | |
|---|---|---|---|---|
| Material | Polymer type* | Number of MA groups/chain** | MA location | MW |
| Ethylene/Maleic anhydride/Propylene Copolymer 1 (EMP 1) | EP:PP 45:55 | 7 | Pendant | 42,000$^a$ |
| Ethylene/Maleic anhydride/Propylene Copolymer 2 (EMP 2) | EP:PP 45:55 | 2 | Pendant | 12,000$^a$ |

TABLE 1-continued

Materials used

| Material | Polymer type* | Number of MA groups/chain** | MA location | MW |
|---|---|---|---|---|
| Ricon 131 MA10[c] | — | 5 | Backbone | 5000[b] |
| MQ[d] + polyisobutylene | — | — | — | — |
| SIBS[e] + Polyisobutylene | — | — | — | — |
| Polyamide | — | — | — | — |
| Polyacrylate | — | — | — | — |

*EP:PP = ethylene to propylene ratio
**MA = Maleic Anhydride, number of groups per chain based on manufacturer's weight percentage
[a]Weight average molecular weight as reported by the manufacturer
[b]Number average molecular weight as reported by the manufacturer
[c]Polybutadiene adducted with maleic anhydride
[d]Trimethylsiloxysilicate
[e]Styrene isoprene butadiene block copolymer The lip color prototypes for the transfer resistance test were generated by heating the above materials to 80° C. and combined with (1) an appropriate solvent (Isododecane), and (2) a pigment. The materials were then blended with an amine functional material as follows:

TABLE 2

Lip Color Prototypes

| Material Blend | Maleated Material (wt %) | Aminated Material (wt %) | Solvent (wt %) | Pigment (wt %) |
|---|---|---|---|---|
| EMP 1 | 45 | 0 | 45 | 10 |
| EMP 1/amino propyl polydimethylsiloxane* | 40.5 | 10 | 40.5 | 9 |
| EMP 1/amino propyl polydimethylsiloxane* | 44.1 | 2 | 44.1 | 9.8 |
| EMP 2 | 45 | 0 | 45 | 10 |
| EMP 2/amino propyl polydimethylsiloxane* | 36 | 20 | 36 | 8 |
| Ricon 131 MA10 | 45 | 0 | 45 | 10 |
| Ricon 131 MA10/ amino propyl polydimethylsiloxane | 36 | 20 | 36 | 8 |
| Ricon 131 MA10/ amodimethicones | 43 | 5 | 43 | 9 |

*Invention

Vitro-Skin®, rough side up, was placed on a vacuum plate and the vacuum plate was turned on. Then a thin (1 to 3 mil), uniform film of each of the above noted lip color prototypes were drawn down on separate portions of the Vitro-Skin surface. The film was allowed to sit at ambient conditions for 1 hour. Using a pipet, three drops of vegetable oil were dropped onto the right side of the dried film. Using another pipet, three drops of water were dropped onto the left side of the dried film. Cosmetic brush applicators were then used to spread the oil and water evenly over their respective portions of the film surface, i.e. right and left, respectively. The oil and water were allowed to remain on the film undisturbed for 15 minutes. Then the excess oil and water were wiped from the film surface using lint free wipers and as little pressure as possible.

Disks were then cut from a clean, white CVS brand Styrofoam dinner plate using a 1.5 inch diameter circular punch. The surface and edges of each disk were smooth and even. Double-sided adhesive tape was used to attach two disks (Disk #1 and Disk #2) to the bottom surface of two 1 kg weights, one disk for each weight. The weights were then placed on top of the film so that Disk #1 was in contact with the oil section of the film. And Disk #2 was in contact with the water section of the film. The 1 kg weight was then carefully rotated 360 degrees over a period of 3-5 seconds while maintaining the discs contact with the film coated substrate. The weight was then lifted straight up off the film surface and the disk was then carefully removed from the weight avoiding damage to the disk.

The substrates and disks were then evaluated for color transfer. The amount transferred was ranked on a scale of 1 to 5 (5=high transfer resistance, 1=low transfer resistance).

TABLE 3

TRANSFER RESISTANCE RESULTS

| Sample No. | Material | Transfer resistance to water and oil |
|---|---|---|
| 1. | EMP 2 | Low ($H_2O$-1, Oil-2) |
| 2. | EMP 2 + amino propyl polydimethylsiloxane (20%) | Medium ($H_2O$-2, Oil-5) |
| 3. | EMP 1 | High ($H_2O$-5, Oil-5) |
| 4. | EMP 1 + amino propyl polydimethylsiloxane (10%) | High ($H_2O$-4, Oil-5) |
| 5. | EMP 1 + amino propyl polydimethylsiloxane (2%) | High ($H_2O$-5, Oil-5) |
| 6. | Ricon 131 MA10 | Medium ($H_2O$-4, Oil-1) |
| 7. | Ricon 131 MA10/amino propyl polydimethylsiloxane | heavily cross linked, not testable |
| 8. | Ricon 131 MA10/amodimethicones | Medium ($H_2O$-3, Oil-1) |
| 9. | MQ | Medium ($H_2O$-3, Oil-2) |
| 10. | SIBS | Medium ($H_2O$-3, Oil-3) |
| 11. | Polyamide | High ($H_2O$-4, Oil-5) |
| 12. | Polyacrylate | Low ($H_2O$-1, Oil-1) |

The transfer tests results within Table 3 above demonstrate the enhanced performance of the materials containing maleic anhydride as a pendant group on the copolymer upon reactive blending with amodimethicone. Contrarily, maleic functional polymers having the maleic anhydride molecule within the backbone were not able to form a two-phase liquid upon blending. At the low quantities of amodimethicone able to be incorporated with main chain maleics, the improvement in transfer resistance was not observable in these polymers.

Example 2

Flexibility Testing

To compare the comfort of a few materials in Example 1, a flexibility test methodology was validated. Several Avon and competitor lip products, listed in Table 4 below, were cast on a rubber substrate in a 1×1 sq. inch area, such that 20 mg of solids remain behind after drying. The rubber substrate was pulled to 3 times their length and dusted using a nail polish brush. The sample was then re-weighed and the weight loss was plotted against the consumer comfort, as shown in FIG. 1. FIG. 1 demonstrates that higher weight loss (less flexibility) leads to less comfort for the consumer.

TABLE 4

PRODUCTS DISPLAYED IN FIG. 1

| Product | Weight Loss % |
|---|---|
| Covergirl Outlast Smoothwear | −1.9 |
| Covergirl Outlast All Day | 1.0 |
| L'Oreal Infallible | −5.8 |
| Revlon Colorstay Ultimar Liq Lip Color | 7.2 |
| Avon PW Liquid Lip Color | −2.0 |
| Avon PW Lipstick | −2.3 |

TABLE 4-continued

PRODUCTS DISPLAYED IN FIG. 1

| Product | Weight Loss % |
|---|---|
| Revlon colorstay overtime | 10.0 |
| L'Oreal Endless | 9.0 |

Consequently, flexibility testing of variations of EMP 1, noted by Samples 1 through 3 in Table 5, was compared to the internal benchmarks, noted by Samples 4 through 7 in Table 5. The flexibility testing was done in accordance with the above-noted protocol.

TABLE 5

RESULTS OF FLEXIBILITY TESTING

| Sample No. | Material | Average Weight loss | Expected comfort |
|---|---|---|---|
| 1. | EMP 1 | 1.45% | High |
| 2. | EMP 1 with 10% amino propyl polydimethylsiloxane | 0.09% | High |
| 3. | EMP 1 with 2% amino propyl polydimethylsiloxane | −4.17% | High |
| 4. | MQ | 7% | Medium |
| 5. | SIBS | 19% | Low |
| 6. | Polyamide | 8% | Medium |
| 7. | Polyacrylate | 9% | Medium |

The EMP 1 showed less weight loss as compared to the internal benchmark film formers, which was improved upon by reactively blending the EMP 1 with amino propyl polydimethylsiloxane. Thus, it was demonstrated that reactive blends are expected to have superior comfort.

Example 3

Tack Testing

Lip products were applied to two separate pieces of Vitro-Skin® and the force required to pull them apart was recorded as Tack Force using a Texture Analyzer TA-XT, simulating how consumers perceive lip product tackiness. The temperature was controlled at 34° C. using a Peltier Plate correlating with lip temperature. A small diameter probe (1 inch) was used to minimize variation. The Vitro-Skin® was attached to 3M Double Side polyethylene foam tape (1/32 inch) to replicate the lip's cushioning texture. Lip products (0.0090-0.0100 g) applied to Vitro-Skin® were attached to Texture Analyzer TA-XT platform and upper probe. The experiment was performed using the following measurement parameters:
Force: 100 g
Dwell time: 10 sec
Test Speed: 0.1 mm/sec
Post Speed: 5 mm/sec

TABLE 5

RESULTS OF TACK TESTING

|  | Tack g time = 0 | Decrease at t = 0 |
|---|---|---|
| EMP 2 | 525.840 |  |
| EMP 2 with 20% amino propyl polydimethylsiloxane | 181.307 | 65% |

TABLE 5-continued

RESULTS OF TACK TESTING

|  | Tack g time = 0 | Decrease at t = 0 |
|---|---|---|
| EMP 1 | 301.486 |  |
| EMP 1 with 10% amino propyl polydimethylsiloxane | 207.519 | 31% |

Upon reactively blending Marlene with amine-functional dimethicones, tack was decreased by at least 31% (EMP 1) and 65% (EMP 2) in initial (t=0) tack All references including patent applications and publications cited herein are incorporated herein by reference in their entirety and for all purpose to the same extent as if each individual publication or patent or patent application was specifically and individually indicated to be incorporated by reference in its entirety for all purposes. Many modifications and variations of this invention can be made without departing from its spirit and scope, as will be apparent to those skilled in the art. The specific embodiments described herein are offered by way of example only, and the invention is to be limited only by the terms of the appended claims, along with the full scope of equivalents to which such claims are entitled.

The invention claimed is:

1. A cosmetic composition for application to an integument comprising, in a suitable cosmetic vehicle, a first phase polymer having pendant maleic anhydride functional groups and a second phase polymer having complementary reactive functional groups, wherein the first phase polymer and second phase polymer are reactively blended to form a two phase copolymer blend film that provides a durability benefit through an interfacial chemical reaction, wherein the second phase polymer is a polymer of the structure of II:

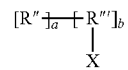

II where R″ and R‴ are monomer units independently selected from any synthetic monomers; b is at least 2; a+b are such that the $M_w$ of the compound is between 500 and 1,000,000 Daltons; and X is a functional group chosen from either hydroxyl or amine.

2. The cosmetic composition of claim 1, wherein the first phase polymer is a polymer of the structure of Formula I:

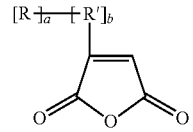

wherein R and R' are monomer units independently selected from the group consisting of propylene, ethylene, styrene, methacrylate, ester, fluoropolymer, urethane, or any carbon monomer; b is at least 2; and a+b are such that the $M_w$ of the compound is between 500 and 1,000,000 Daltons.

3. The cosmetic composition of claim 2, wherein a+b is such that the $M_w$ of the first phase polymer is between about 5,000 to about 100,000 Daltons.

4. The cosmetic composition of claim 3, wherein a+b is such that the $M_w$ of the first phase polymer is between about 10,000 to about 50,000 Daltons.

5. The cosmetic composition of claim 2, wherein R and R' are different.

6. The cosmetic composition of claim 5, wherein R is ethylene and R' is propylene.

7. The cosmetic composition of claim 2, wherein the ratio of R to R' is about 40:60 to about 90:10.

8. The cosmetic composition of claim 7, wherein the ratio is about 45:55 to about 75:25.

9. The cosmetic composition of claim 1, wherein the maleic anhydride content of the first phase polymer is about 0.1-20% by weight.

10. The cosmetic composition of claim 9, wherein the maleic anhydride content is about 1-10% by weight.

11. The cosmetic composition of claim 10, wherein the maleic anhydride content is about 2-5% by weight.

12. The cosmetic composition of claim 1, wherein the synthetic monomer is a siloxane.

13. The cosmetic composition of claim 1, wherein complementary reactive functional group content of the second phase polymer is about 0.1-50% by weight of the second phase polymer.

14. The cosmetic composition of claim 13, wherein the complementary reactive functional group content is about 1-20% by weight.

15. The cosmetic composition of claim 14, wherein the complementary reactive functional group content is about 2-10% by weight.

16. The cosmetic composition of claim 1, wherein the first phase polymer has less than about 10% crystallinity.

17. The composition according to claim 1, wherein the composition is further comprised of additional ingredients selected from the group consisting of sunscreens, pigments, other film formers, thickeners, retinoids, waxes, emollients, long wearing particles/pigments, and compatible combinations thereof.

18. The cosmetic composition of claim 1, wherein the durability benefit is selected from long wear, enhanced transfer resistance, enhanced shine, and/or prolonged exposure to actives.

19. The cosmetic composition of claim 1, wherein the first phase polymer and second phase polymer are reactively blended prior to formulation.

20. A method for imparting a transfer-resistant film on a human integument comprising applying to said human integument an effective amount of the cosmetic composition of claim 1.

21. The method of claim 20, wherein the first phase polymer and second phase polymer are applied sequentially to the integument and the interfacial reaction occurs during application.

22. A kit comprising a lip product and a cosmetic composition of claim 1.

23. The kit of claim 22, wherein the first phase polymer and second phase polymer are separate components in the kit.

* * * * *